United States Patent
Setford et al.

(10) Patent No.: US 9,810,657 B2
(45) Date of Patent: Nov. 7, 2017

(54) ELECTROCHEMICAL SENSORS AND A METHOD FOR THEIR MANUFACTURE

(75) Inventors: Steven John Setford, Fortrose (GB); Scott J. Sloss, Inverness (GB)

(73) Assignee: Cilag GmbH International, Zug (CH)

( * ) Notice: Subject to any disclaimer, the term of this patent is extended or adjusted under 35 U.S.C. 154(b) by 668 days.

(21) Appl. No.: 14/002,956

(22) PCT Filed: Sep. 7, 2012

(86) PCT No.: PCT/GB2012/052218
§ 371 (c)(1),
(2), (4) Date: Sep. 3, 2013

(87) PCT Pub. No.: WO2014/037688
PCT Pub. Date: Mar. 13, 2014

(65) Prior Publication Data
US 2014/0311903 A1    Oct. 23, 2014

(51) Int. Cl.
*G01N 27/327*    (2006.01)

(52) U.S. Cl.
CPC ................ *G01N 27/3272* (2013.01)

(58) Field of Classification Search
CPC .......... G01N 27/3272; B01L 3/502715; B01L 3/502707; B01L 3/502723; B01L 2300/0887; B01L 2300/0636
See application file for complete search history.

(56) References Cited

U.S. PATENT DOCUMENTS

| | | | |
|---|---|---|---|
| 6,071,391 A * | 6/2000 | Gotoh | C12Q 1/005 204/403.05 |
| 6,179,979 B1 | 1/2001 | Hodges et al. | |
| 6,193,873 B1 | 2/2001 | Ohara et al. | |
| 6,284,125 B1 | 9/2001 | Hodges et al. | |
| 6,413,410 B1 | 7/2002 | Hodges et al. | |
| 6,596,112 B1 | 7/2003 | Ditter et al. | |
| 6,620,310 B1 | 9/2003 | Ohara et al. | |
| 6,676,995 B2 | 1/2004 | Dick et al. | |
| 6,716,577 B1 | 4/2004 | Yu et al. | |
| 6,749,887 B1 | 6/2004 | Dick et al. | |
| 6,797,150 B2 | 9/2004 | Kermani et al. | |
| 6,830,934 B1 | 12/2004 | Harding et al. | |
| 6,863,801 B2 | 3/2005 | Hodges et al. | |
| 6,872,298 B2 | 3/2005 | Kermani | |

(Continued)

FOREIGN PATENT DOCUMENTS

| | | |
|---|---|---|
| CN | 101779120 A | 7/2010 |
| JP | H10-78407 A | 3/1998 |

(Continued)

OTHER PUBLICATIONS

International Preliminary Report on Patentability issued in related International Patent Application No. PCT/GB2012/052218, dated Mar. 10, 2015, 8 pages.

(Continued)

*Primary Examiner* — Gurpreet Kaur

(57) ABSTRACT

The invention provides electrochemical-based modules useful for the determination of an analyte in a bodily fluid sample. The modules of the invention provide opposed electrodes, but the contact areas for making electrical contact between the electrodes and the analyte measurement device are coplanar.

16 Claims, 6 Drawing Sheets

(56) References Cited

U.S. PATENT DOCUMENTS

| | | |
|---|---|---|
| 7,045,046 B2 | 5/2006 | Chambers et al. |
| 7,288,174 B2 | 10/2007 | Cui et al. |
| 7,291,256 B2 | 11/2007 | Teodorczyk et al. |
| 7,498,132 B2 | 3/2009 | Yu et al. |
| 7,749,371 B2 | 7/2010 | Guo et al. |
| 7,846,312 B2 | 12/2010 | Hodges et al. |
| 8,182,747 B2 | 5/2012 | Marquant et al. |
| 2007/0138026 A1* | 6/2007 | Fujiwara ............ A61B 5/14546 205/777.5 |
| 2009/0026074 A1* | 1/2009 | Iyengar .............. G01N 27/3272 204/400 |
| 2009/0317297 A1 | 12/2009 | Mahoney et al. |
| 2011/0073493 A1 | 3/2011 | Chatelier et al. |
| 2012/0267245 A1 | 10/2012 | Chatelier et al. |
| 2013/0161204 A1* | 6/2013 | Uchiyama ................ C12Q 1/32 205/777.5 |
| 2013/0228474 A1 | 9/2013 | Sloss et al. |

FOREIGN PATENT DOCUMENTS

| | | |
|---|---|---|
| JP | H11-255204 A | 9/1999 |
| JP | 2004132961 A | 4/2004 |
| JP | 2004515784 A | 5/2004 |
| JP | 2005003679 A | 1/2005 |
| JP | 2010008411 A | 1/2010 |
| JP | 2015508900 A | 3/2015 |
| WO | WO 03/056345 | 7/2003 |
| WO | WO 2009/015292 | 1/2009 |
| WO | WO 2010/095787 | 8/2010 |
| WO | 2012042903 A1 | 4/2012 |

OTHER PUBLICATIONS

International Search Report, International patent application No. PCT/GB2012/052218, dated Jun. 6, 2013, European Patent Office, Rijswijk, Netherlands, 4 pages.

First Office Action issued in related Chinese Patent Application No. 201280075675.1, dated May 4, 2016, 18 pages.

Notice of Reasons for Rejection issued in related Japanese Patent Application No. 2015-530487, dated Jul. 19, 2016, 7 pages.

* cited by examiner

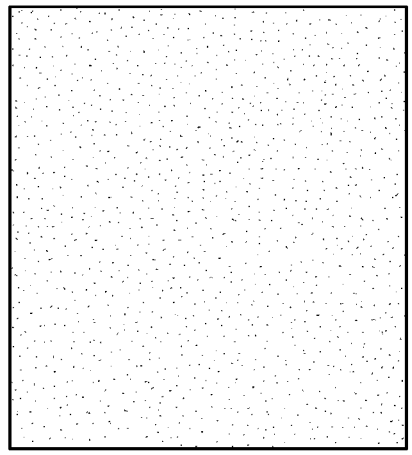
FIG. 5A
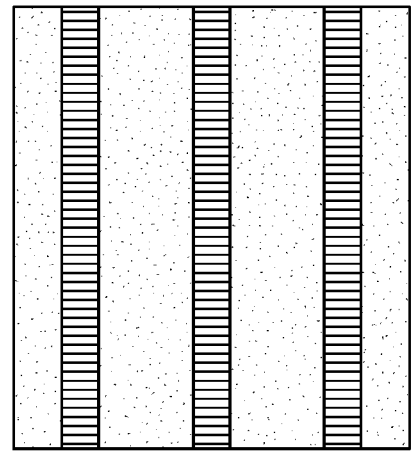
FIG. 5B
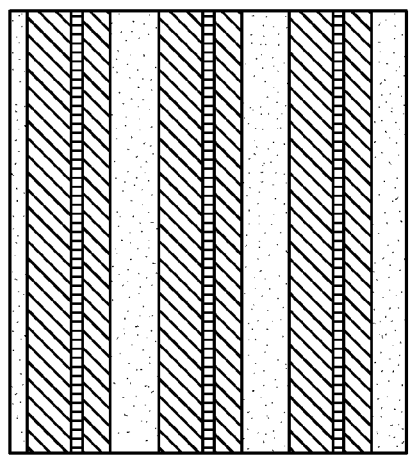
FIG. 5C
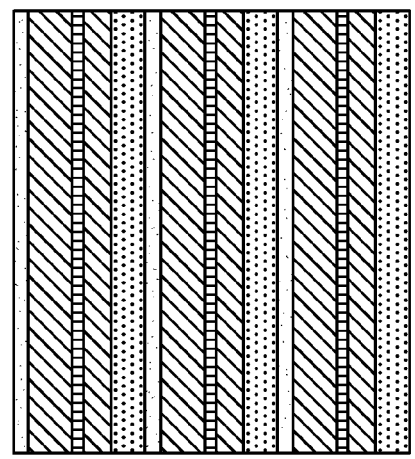
FIG. 5D
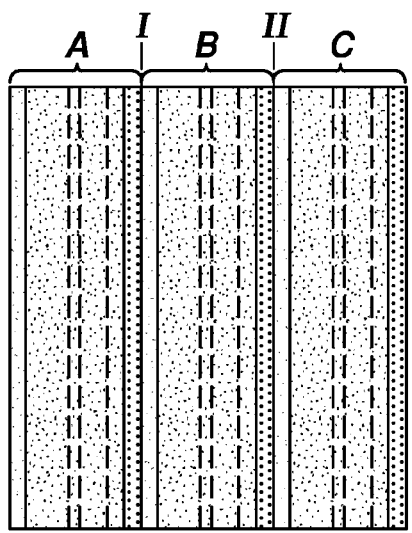
FIG. 5E
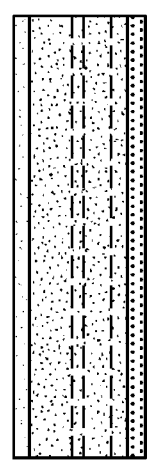
FIG. 5F
FIG. 5G

ELECTROCHEMICAL SENSORS AND A METHOD FOR THEIR MANUFACTURE

This application claims the benefits under 35 USC §§119 and 371 of International Application Number PCT/GB2012/052218, filed on Sep. 7, 2012, which is incorporated by reference in its entirety herein this application.

FIELD OF THE INVENTION

The present invention relates to electrochemical sensors and methods for manufacturing the sensors. In particular, the invention relates to sensors with opposed electrodes, but coplanar contact points for purposes of electrical contact between the sensors and an analyte measurement device.

BACKGROUND OF THE INVENTION

Methods and devices for the analyte detection and concentration measurement in a fluid sample are well known. For example, various devices and methods are known for determining glucose, ketone bodies, cholesterol, lipoproteins, triglycerides, acetaminophen or HbA1c concentrations in a sample of a bodily fluid such as urine, blood, plasma or interstitial fluid. Such determinations can be achieved using analytical test strips, based on, for example, visual, photometric or electrochemical techniques.

In an electrochemical technique, a fluid sample is placed into a sample chamber of an electrochemical cell of a sensor that includes at least a counter and working electrode. The analyte reacts with a redox reagent in the cell to form an oxidizable or reducible substance. The quantity of oxidizable or reducible substance may be electrochemically determined and related to the amount of the analyte present in the sample.

In the case of the measurement of glucose in a blood sample, the measurement may be based on the selective oxidation of glucose by means of an enzyme. For example, the enzyme glucose oxidase catalyzes the oxidation of glucose to gluconic acid by transfer of electrons from the glucose molecule to a prosthetic group embedded within the enzyme structure. This prosthetic group, now in a reduced state may be re-oxidized by addition of a suitable mediator which in turn assumes a reduced state. Conducting these reactions within an electrochemical cell with a test voltage applied between two electrodes creates an output current by the electrochemical re-oxidation of the reduced mediator at the electrode surface. In an ideal environment, stoichiometric principles dictate that the amount of reduced mediator created during the enzymatic reaction is directly proportional to the amount of glucose present in the sample. Therefore, the test current generated is directly proportional to the concentration of glucose in the sample. The current generated may be detected by an analyte measurement device, such as a test meter, used in conjunction with the electrochemical cell or test strip and converted into a glucose concentration reading using an algorithm that relates the test current to a glucose concentration via a simple, mathematical relationship. Conventional electrochemical-based analytical test strips are described in, for example, U.S. Pat. Nos. 6,179,979, 6,193,873, 6,284,125, 6,716,577, 6,749,887, 6,797,150, 6,863,801, 6,872,298, 7,045,046, 7,498,132, 7,846,312, 6,413,410 and 7,749,371 each of which is hereby incorporated in its entirety by reference.

Sensors for use in analyte testing, in which electrochemical cells are incorporated, typically use a carrier material to provide structural integrity and facilitate handling. The carrier materials may take any form, but typically are in the form of a test strip. The costs of sensor manufacture are related to the materials used and certain cost benefits accrue from reducing the quantities of specialized materials used in constructing the test strips, such as by using specialized materials in constructing only the electrochemical cell. However, manipulation of sensors that primarily constitute an electrochemical cell present challenges to end-users due to the resulting reduced size. Additionally, a small-sized strip or sensor increases the potential for contaminating the port of the meter, into which the sensor is placed, with the fluid being analyzed. Therefore, it is desirable for purposes of cost and manipulation to construct sensors having a reduced dimension wherein only the electrochemical cell component is made from specialized materials.

BRIEF DESCRIPTION OF THE DRAWINGS

FIGS. 5A through 5G depict various stages of production of one embodiment of an ECM of the invention.

DETAILED DESCRIPTION OF THE INVENTION

Figure 1A:
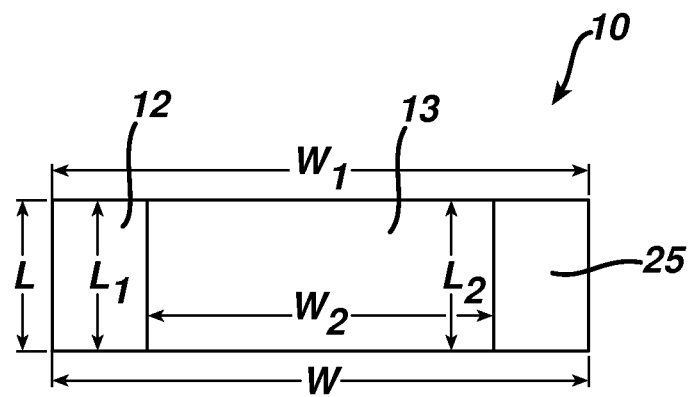
FIG. 1A is a top, plan view of an ECM of the invention.

In general, the invention provides electrochemical-based sensors in the form of electrochemical modules ("ECMs") useful for the determination of an analyte in a bodily fluid sample. The modules of the invention provide opposed electrodes, but the contact areas for making electrical contact between the electrodes and the analyte measurement device are coplanar. The modules of the invention are advantageous in that they are of a small size reducing manufacturing costs and facilitating incorporation of the ECMs into spools, cartridges or the like for purposes of feeding the ECMs into, or manipulating the ECMs within, an analyte measurement device, which eliminates the need for user handling. Additionally, the ECMs of the invention may be conveniently manufactured using a continuous web-based process.

The invention provides ECMs comprising, consisting essentially of, and consisting of: a first substrate having a first conductive layer thereon and forming a first substrate-conductive layer assembly wherein the assembly has a first width and length; a second substrate having a second conductive layer thereon and forming a second substrate-conductive layer assembly wherein the assembly has a second width that is less than the first width and a second length that is substantially the same as the first length, the first and second conductive layers being in a facing relationship; a first and a second spacer disposed between the first and second assemblies and maintaining the assemblies in a spaced apart relationship; a chamber formed between the first and second assemblies and configured to receive a fluid sample, the chamber comprising a reagent capable of reacting with an analyte in the fluid sample; and a third spacer adjacent to one of the first or second spacers, a surface of the third spacer comprising a conductive layer that is in electrically conductive contact with the second conductive layer. In another embodiment, the invention provides ECMs comprising, consisting essentially of, and consisting of: a first substrate having a first conductive layer thereon, the first conductive layer comprising a first and second portion having a gap therebetween, the first substrate and first conductive layer forming a first substrate-conductive layer assembly wherein the assembly has a first width and length; a second substrate having a second conductive layer thereon and forming a second substrate-conductive layer assembly wherein the assembly has a second width that is less than the first width and a second length that is substantially the same as the first length wherein the first and second conductive layers are in a facing relationship; a first and a second spacer disposed between the first and second assemblies and maintaining the assemblies in a spaced apart relationship; a chamber formed between the first and second assemblies and configured to receive a fluid sample, wherein the chamber comprises a reagent capable of reacting with an analyte of the fluid sample; and an electrically conductive third spacer adjacent to one of the first or second spacers, wherein the third spacer is in contact with the gap and in electrically conductive contact with the first and second conductive layers. Additionally, methods of manufacturing the ECM of the invention are provided.

Figure 1B:
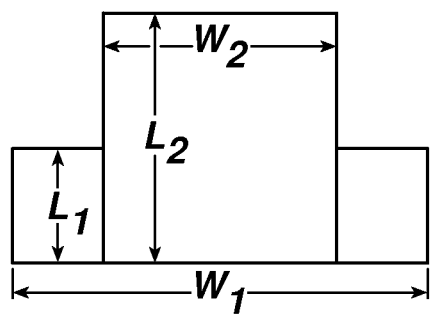
FIG. 1B is a top plan view of another embodiment of an ECM of the invention.

Although the ECM of the invention may have a variety of shapes, it is preferred that the ECM be of a rectangular shape with the width ("W") of the ECM being greater than the length ("L") as shown in FIG. 1A. However, as will be understood from the discussion below regarding contact areas between the ECM and the analyte measurement device with which the ECM will be used, other configurations are possible and within the scope of this invention, for example as shown in FIG. 1B.

Figure 2A:
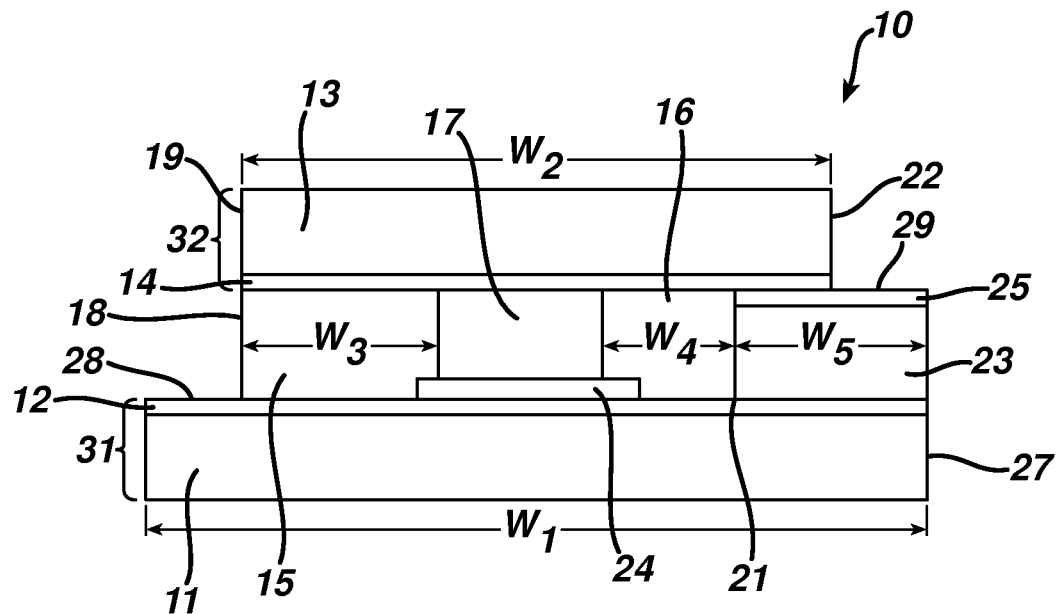
FIG. 2A is a side view of the ECM of FIG. 1A.
Figure 2B:
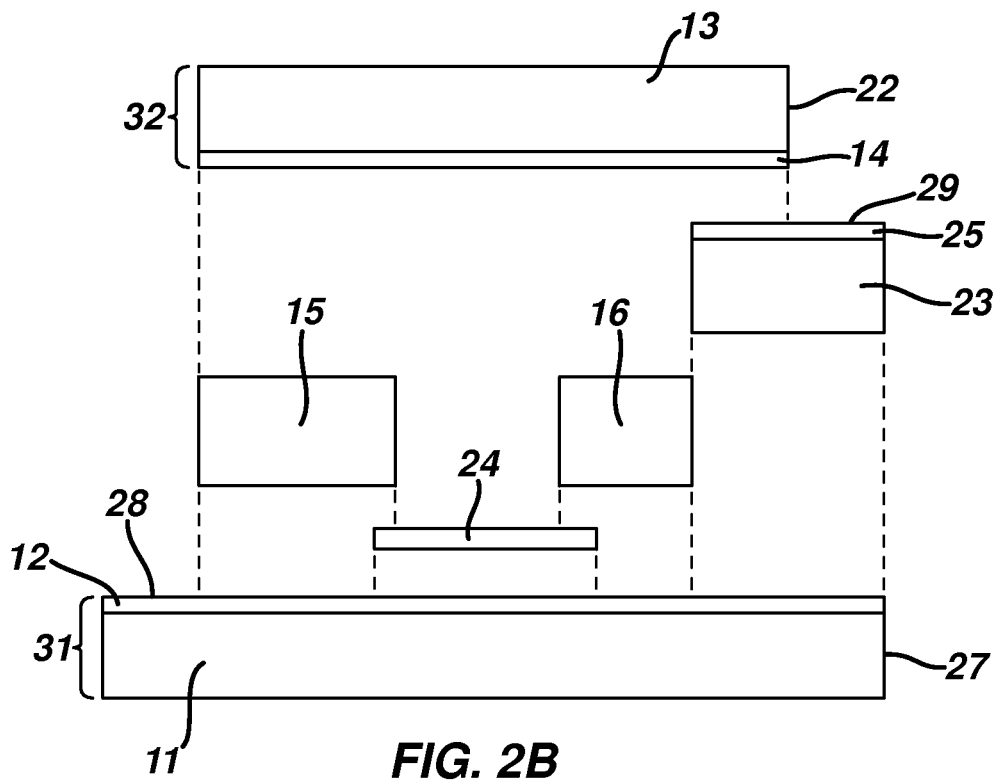
FIG. 2B is an exploded view of the ECM of FIG. 2A.

Referring to FIGS. 1A, 2A and 2B, ECM 10 is shown with a first substrate 11, which is composed of a non-conductive material. First conductive layer 12 is provided on one surface of substrate 11 and layer 12 and substrate 11 form a first substrate-conductive layer assembly 31. Second substrate 13 formed from a non-conductive material also is shown on one surface of which is provided second conductive layer 14. Second substrate 13 and second conductive layer 14 form second substrate-conductive layer assembly 32. First and second conductive materials 12 and 14 form the electrodes of the ECM and preferably extend across the entire width and length of the respective substrates on which they are provided. Preferably, and as shown, first and second conductive materials 12 and 14 are in a facing relationship. Also preferably, one of the substrate-conductive layer assemblies, as shown substrate 11 and conductive layer 12, has a width ("$W_1$") that is greater than that ("$W_2$") of the other substrate-conductive layer assembly. In the embodiment shown and preferably, the length ("$L_1$") of the first substrate-conductive layer assembly is substantially the same as that ("$L_2$") of the second substrate-conductive layer assembly.

Spacers 15 and 16, composed of non-conductive materials, are interposed between the facing surfaces of conductive layers 12 and 14 and serve to maintain the conductive materials in a spaced-apart relationship. Of note and preferably, is that one spacer, spacer 15 as shown, has a width ("$W_3$") greater than that ("$W_4$") of the other spacer 16. The lengths of the spacers may be different, but preferably are the same. The spacers also define the sidewalls of a chamber 17, the top and bottom of which chamber are formed by the substrate-conductive layer assemblies. The chamber receives a fluid to be analyzed and, thus, the dimensions of the spacers must be selected so that the desired chamber size is obtained.

For convenience and purposes of orientation, the first substrate-conductive layer assembly 31 will be considered to be the bottom and the second substrate-conductive layer 32 will be considered to be the top of the ECM. However, these terms are not meant to limit these layers to a particular orientation.

As shown spacer 15 is preferably positioned so that its first latitudinal end 18 is positioned in substantial alignment with first latitudinal end 19 of the top substrate-conductive layer assembly 32. However, the latitudinal end 21 of second spacer 16 is positioned so that a gap is formed between it and latitudinal end 22 of the top substrate-conductive layer assembly 32. Immediately adjacent to latitudinal end 21 of spacer 16 is a third spacer 23. Preferably, there is substantially no gap between third spacer 23 and spacer 16. Spacer 23 is composed of a non-conductive material and has a third conductive layer 25 on one surface, which layer 25 faces and is in electrically conductive contact with second conductive layer 14. Third spacer 23 has a width ("$W_5$") such that the latitudinal end 26 of third spacer 23 extends beyond the latitudinal end 21 of the top substrate-conductive layer assembly 32 and is preferably substantially aligned with latitudinal end 27 of the first substrate-conductive layer assembly 31.

Electrical contact between ECM 10 and an analyte measurement device, such as a meter, is provided for at the areas 28 and 29 of first conductive layer 12 and third conductive layer 18, respectively. Thus, areas 28 and 29 are sized and shaped so that the desired reliable, low-resistance contact may be made with the analyte measurement device.

The size and shape of the ECM 10 and its components may be varied to assume any desired configuration. For example, and as shown in FIG. 1B, the ECM may assume a "t"-shaped configuration. In such a configuration, the width of the top and bottom substrate are as described for the ECM 10 of FIG. 1A, but the top has an elongated length. One of ordinary skill in the art will recognize that the dimensions of the other components of the ECM of FIG. 1B will be adjusted to achieve the desired result.

Preferably, however, the ECM is shaped substantially similar to FIG. 1A and more preferably the width of ECM 10, at its widest portion, is about 3 mm to about 48 mm, and more preferably about 6 mm to about 10 mm, and the length is about 0.5 mm to about 20 mm, more preferably about 1 to 4 mm. The distance between the top conductive layer and the bottom conductive layer will vary depending on the desired chamber size. Preferably, the chamber is of a size such that the fluid volume the chamber may hold is from about 0.1 micro-liters to about 5 micro-liters, more preferably about 0.2 to about 3 micro-liters and most preferably about 0.2 to about 0.4 micro-liters. Preferably, the thicknesses of spacers 15 and 16 are suitable to achieve the desired chamber volume and more preferably may be about 1 microns to about 500 microns, yet more preferably 10 to about 400 microns, still more preferably about 25 to about 200 microns and most preferably about 50 to about 150 microns. The chamber aperture created by the spacers 15 and 16 may be of any desired dimension but preferably is between about 1.00 and about 1.75 mm.

Substrates 11 and 13 are of any size and shape that achieves the desired ECM configuration. The thickness of the substrates preferably are between about 50 microns to about 200 microns in thickness, preferably about 100 to about 175 microns. The substrates are composed of any suitable electrically-insulating, non-conducting material and, preferably, the material selected has a coefficient of thermal expansion sufficiently small so that the resulting substrate layers do not adversely affect the chamber volume. Suitable materials include, for example, a nylon substrate, polycarbonate substrate, a polyimide substrate, a polyvinyl chloride substrate, a polyethylene substrate, a polypropylene substrate, a glycolated polyester substrate, a polyester substrate, ceramic, glass or the like and combinations thereof. The substrates are preferably formed of polyethylene terephthalate ("PET"). Optionally, the substrates may contain one or more fillers to control physical properties. The top substrate layer is preferably wholly or partially translucent or transparent, or includes a translucent or transparent window, so that filling of the strip chamber with the fluid to be analyzed may be seen by the user. Although, for the purpose of explanation only, ECM 10 has two conductive layers forming two electrodes, and one chamber therein the ECM may be designed to include any suitable number of electrodes, chambers and conductive layers.

First and second conductive layers 12 and 14 may be deposited on substrate 11 by any suitable deposition method including thin film deposition, sputtering, spray coating, electro-less plating, thermal evaporation, printing methods including screen printing, and the like and combinations thereof. Conductive layers 12 and 14 are formed from any suitable, electrically conductive material including, metals such as gold, palladium, platinum, tin-oxide, iridium, indium, and titanium-palladium alloys and non-metals including electrically carbon-based materials with or without electro-catalytic materials, graphene and the like and combinations thereof. Preferably, the material is a metal and more preferably, one of the conductive layers is formed of palladium and the other is formed of gold, and more preferably the conductive layer on which the reagent is deposited is gold and the other is palladium or both are gold. A preferred deposition method of these materials is by sputtering. The conductive layers may be of any suitable thickness. If a thick film is desired, the thickness typically will be about 5 to 20 mm. If a thin film is desired, the thickness will be about 10 to about 100 nanometers.

The reagent 24 as shown is disposed on one of the conductive layers, but may be disposed on multiple surfaces of the chamber. The reagent may cover an area of any desired dimensions, but in ECM 10 as shown in FIG. 1A the reagent will have a width of between about 1 and 4 mm and preferably about 2.25 to 3 mm, a length of about 2 to about 3.5 microns, and a height to about 2 to about 10 microns. The reagent may be any reagent useful in carrying out the analyte analysis desired and may be formed from various materials including mediators, enzymes and the like and combinations thereof. Preferably, the reagent will be of a formulation that is capable of recognizing one or more specific target analytes for example, a biological marker molecule in a fluid sample, Thus, the reagent may include enzyme such as redox enzyme and enzymes requiring cofactors for the oxidation or reduction of analyte species and more specifically may include glucose oxidase, glucose dehydrogenase ("GDH") containing a pyrroloquinone cofactor, GDH containing a nicotinamide adenine dinucleotide cofactor, or a GDH containing a flavin adenosine dinucleotide. Additionally, the reagent may include, antibodies, and other binding ligands such as receptors as well as species that facilitate electrochemical determination of the analytes including redox species, solubilization reagents, buffers, salts, wetting agents such as surfactants and other ionic and non-ionic species. A preferred reagent will contain reagents capable of determining metabolites such as glucose, lactate, ketone bodies, cholesterol and the like. An exemplary reagent formulation is described in U.S. Pat. No. 7,291,256 incorporated in its entirety herein by reference. The reagent and be deposited by any convenient, known method including slot-coating, dispensing from the end of a tube, ink-jet printing, and screen-printing. Suitable exemplary processes are described in U.S. Pat. Nos. 6,749,887; 6,676,995; and 6,830,934 all incorporated in their entireties herein by reference.

Spacers 15, 16 and 23 may be of any suitable thickness and typically will be between about 25 to about 200 microns in thickness, more preferably between about 70 and about 110 microns. The spacers may be formed from a suitable non-conductive material and preferably from such a material that exhibits a degree of flexibility suitable for use in web-based manufacturing. Suitable electrically resistive materials which may be preferred include materials such as polyesters, polystyrenes, polycarbonates, polyolefins, polyethylene terephthalate, glasses, ceramics, mixtures and the like and combinations thereof. Preferably, the material used is MELINEX®, available from Du Pont, with double-sided coatings of a heat activated adhesive, more preferably with double-sided coating of ARCare™ 90503 available from Adhesives Research. A separate adhesive layer, preferably heat activated adhesive and more preferably ARCare™ 90503 may be applied to attach the spacer to the conductive layers.

Alternatively, the spacers may function as a double-sided adhesive to adhere the top and bottom surfaces of the spacers to the conductive material layers. Thus, the spacers may be formed of an electrically resistive material with an adhesive property. Suitable adhesives include, for example, heat activated adhesives, pressure sensitive adhesives, heat cured adhesives, chemically cured adhesives, hot melt adhesives, hot flow adhesives, and the like. Suitable adhesive include those described in U.S. patent application Ser. No. 12/570, 268 which is incorporated in its entirety herein by reference. Pressure sensitive adhesives may be preferred for use in certain embodiments where simplification of fabrication is desired, but the tackiness of pressure sensitive adhesives may result in fabrication tool gumming or product tackiness. In such embodiments, heat or chemically cured adhesives are generally preferred. Especially preferred are the heat-activated and heat-cured adhesives that can be conveniently activated at the appropriate time.

A hot melt adhesive, which is a solvent-free thermoplastic material that is solid at room temperature and is applied in molten form to a surface to which it adheres when cooled to a temperature below its melting point, may also be used. Polyester hot melt adhesives preferred, available, for example, from Bostik Corp. of Middleton, Mass., are linear saturated polyester hot melts exhibiting melting points from about 65° C. up to about 220° C. and range from completely amorphous to highly crystalline in nature. Polyamide (nylon) hot melt adhesives, available from Bostik, may also be used, including both dimer-acid and nylon-type polyamide adhesives. Suitable hot melt adhesive chemistries include ethyl vinyl acetate, polyethylene, and polypropylene.

Lamination techniques may also be used to bond the spacer layers to the conductive layers and suitable lamination techniques are described in U.S. Pat. No. 6,596,112 incorporated herein in its entirety by reference. In general, the layers to be laminated are placed adjacent to each other and heat is applied, whereby a bond between the layers is formed. Pressure may also be applied to aid in forming the bond.

Third conductive layer 25 of third spacer 23 may be formed from the materials as disclosed above for conductive layers 12 and 14. Third conductive layer 25 preferably forms a reliable, low resistance interface with second conductive layer 14. The formation of such an interface provides an electrically conductive contact between layers 25 and 14 and may be accomplished by use of a suitable conductive adhesive as the third conductive layer or as a layer intermediate these surfaces. This intermediate layer may be applied by any suitable means including printing or applying it as a transfer adhesive. More preferably the conductive adhesive is either pressure or temperature activated. If it is printed the layer preferably is between about 5 to about 15 μm in thickness and if transferred on is between about 25 to about 50 μm thick. Alternatively, a reliable interface between conductive layers 25 and 14 is formed by using thermal lamination to provide a fused joint. As yet another alternative, the meter in which the ECM is used may include a contact that applies pressure to the top of substrate 13.

Figure 3A:
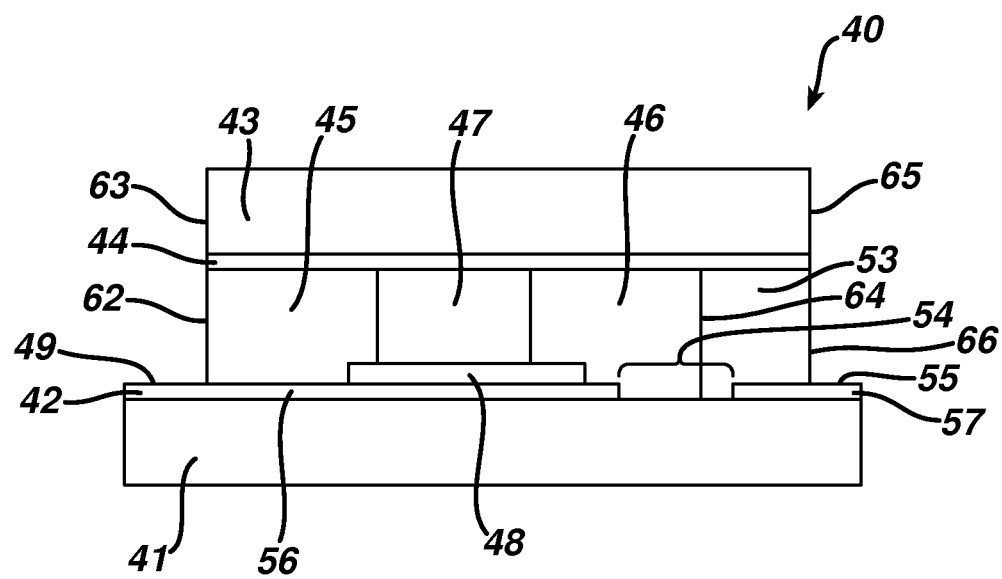
FIG. 3A is a side view of another embodiment of an ECM of the invention.
Figure 3B:
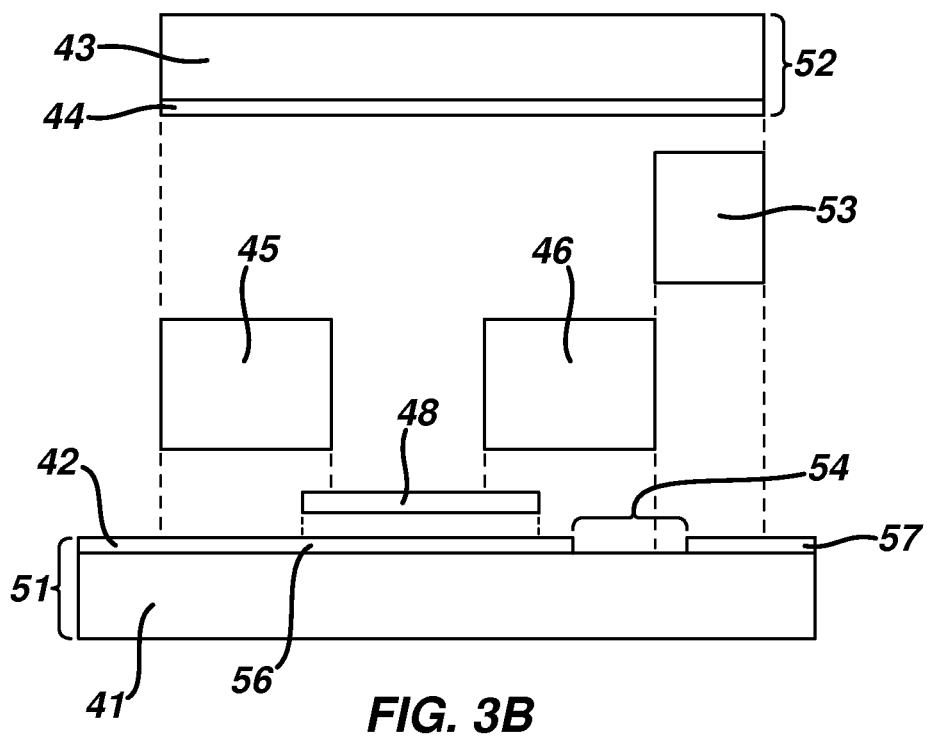
FIG. 3B is an exploded view of the ECM of FIG. 3A.

Referring to FIGS. 3 and 3B, another embodiment of the invention is shown. ECM 40 has a first substrate 41 with first conductive layer 42 is provided on one surface. First conductive layer 42 is composed of two portions 56 and 57 with a gap 54 therebetween that is sufficient to ensure that portions 56 and 57 are isolated from each other so that substantially no electrical conduction occurs between them. Gap 54 may be formed by any convenient method, but preferably is formed by laser ablation of first conductive layer 42. Second substrate 43 also is shown on one surface of which is provided second conductive layer 44, which conductive layer 44 preferably extends across the entire width and length of substrate 43. Preferably, and as shown, first and second conductive materials 42 and 44 are in a facing relationship. Also preferably, one of the substrate-conductive layer assemblies, has a width that is greater than that of the other substrate-conductive layer assembly with the lengths being substantially the same.

Spacers 45 and 46, composed of non-conductive materials, are interposed between conductive layers 42 and 44. A chamber 47 is provided between spacers 45 and 46 and within the chamber is reagent 48. As shown spacer 45 is preferably positioned so that its first latitudinal end 62 is positioned in alignment with first latitudinal end 63 of the top substrate-conductive layer assembly 52. However, the latitudinal end 64 of second spacer 46 is positioned so that a gap is formed between it and latitudinal end 65 of the top substrate-conductive layer assembly 52. Immediately adjacent to latitudinal end 64 of spacer 46 is a third spacer 53 which is conductive. Preferably, there is substantially no gap between third spacer 53 and spacer 46.

Spacer 53 is composed of a suitable conductive material which is in electrically conductive contact with second conductive layer 44 as well as first conductive layer 42. For example, spacer 53 may be applied as a solid, semi-solid or liquid that solidifies in-situ. Exemplary materials include double-sided conductive tape such as 3M 9712 (125 microns), polyester mesh with acrylic adhesive and conductive carbon filler. Conductive spacer 53 has a width such that its latitudinal end 66 is substantially aligned with the latitudinal end 65 of the top substrate-conductive layer assembly 52.

Figure 4:
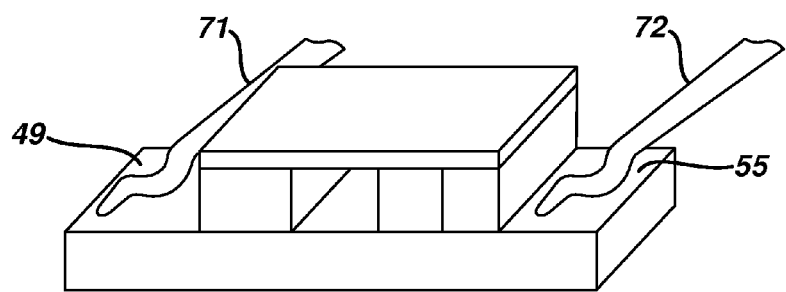
FIG. 4 is an elevated cross-section view of the ECM of FIG. 3A and electrical contact pins for an analyte measurement device.

Electrical contact between ECM 40 and an analyte measurement device, such as a meter, is provided for at areas 55 and 49 of first conductive layer 42. Thus, areas 55 and 49 are sized and shaped so that the desired reliable, low-resistance contact may be made with the analyte measurement device. FIG. 4 depicts ECM and electrical contact pins 71 and 72 of an analyte measurement contacting areas 55 and 49 of ECM 40.

In use, an analyte measurement device will connect to the two electrical contact areas of the ECMs of the invention to form a complete circuit. In one embodiment, a circuit disposed in the measurement device can apply a test potential or current between the two contact areas. In a fluid detection mode, the measurement device will apply a constant current of suitable amperage between the electrodes of the ECM. A fluid sample is delivered to the chamber of the ECM until the chamber is filled. When the fluid sample bridges the gap between the electrodes, the measurement device will measure a voltage decrease below a predetermined threshold resulting in initiation of analyte as described in U.S. Pat. No. 6,193,873 incorporated in its entirety herein by reference. Suitable analyte measurements devices include battery-powered, hand-held meters controlled by on-board micro-processors with circuitry for applying predetermined potentials.

Manufacture of the ECMs of the invention of the invention may be accomplished by any known method. Preferably, a continuous, web process is used for mass production of the ECMs One process is shown in FIGS. 5A through 5G. A metal, such as gold or palladium, is sputter-coated onto one surface of a web of a first substrate material, such as PET, that has a generally elongate, rectangular configuration to provide a conductive film as shown in FIG. 5A. Multiple reagent stripes of the same or different material are dispensed onto portions of the conductive layer as shown in FIG. 5B. Spacers, of unequal width, with or composed of adhesive layers covered by a release liner, are laminated on either side of the reagent as shown in FIG. 5C. The latitudinal end of either spacer does not extend to the latitudinal end of the substrate-metal web. In FIG. 5D is shown a third spacer, one surface of which is has been sputter-coated with a suitable conducting material such as gold, applied adjacent to the spacer that was previously applied and which has the smaller width. The third spacer is applied so that no electrical connection is established with the palladium or gold coated substrate. A second substrate, as seen in FIG. 5E, the inner facing of which is gold coated, is then laminated onto the spacers. The three different tracks, A, B, and C, of ECMs shown in FIG. 5 E may be separated by cutting length-wise along lines I and II to form single continuous tracks of ECMs as shown in FIG. 5F. Each of the continuous tracks in then cut width-wise to form multiple, singulated ECMs as shown in FIG. 5G. Alternatively, a continuous track may be scored width-wise, but not cut, so as to form a continuous ribbon of ECMs each of which may, if required, be torn or cut along the score line for disposal after use.

Figure 6A:
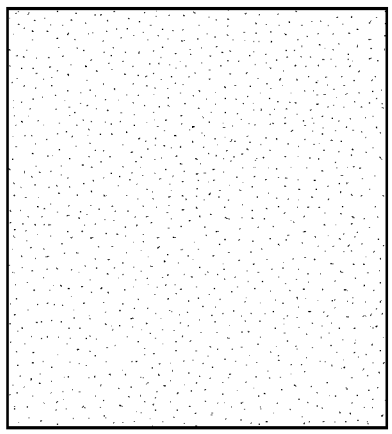
FIGS. 6A through 6H depict various stages of production of a second embodiment of an ECM of the invention.
Figure 6B:
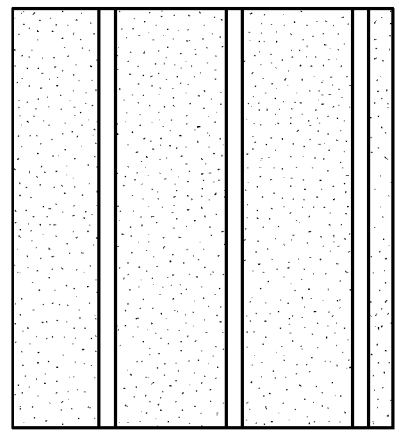
Figure 6C:
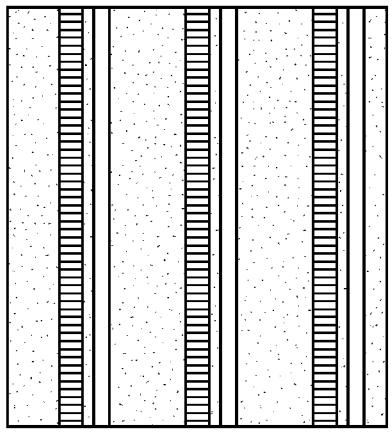
Figure 6D:
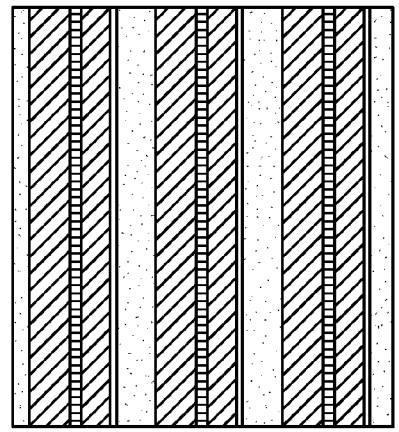
Figure 6E:
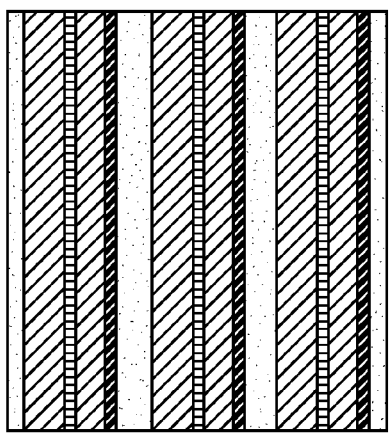
Figure 6F:
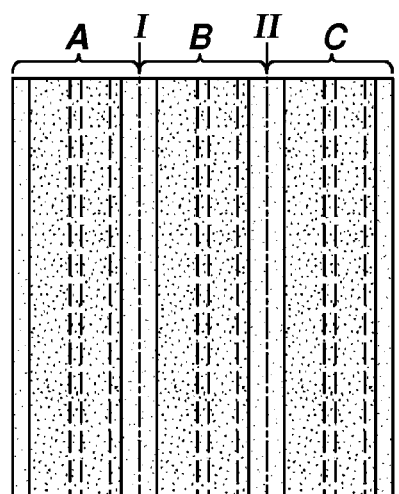
Figure 6G:
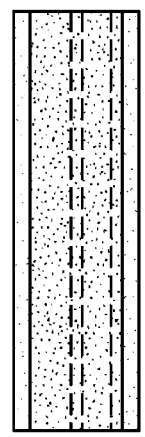
Figure 6H:

Another process for manufacturing ECMs of the invention is shown in FIGS. 6A through 6 H. A conductive film is laminated onto a first substrate material, such as PET, that has a generally elongate, rectangular configuration to provide a conductive film as shown in FIG. 6A. Multiple length-wise areas of the conductive surface are laser ablated to strip the conductive film from those areas as shown in FIG. 6B. Multiple reagent strips of the same or different material are dispensed onto portions of the conductive layer as shown in FIG. 6C. Non-conductive spacers, of unequal width, with or composed of adhesive layers covered by a release liner are laminated on either side of the reagent as shown in FIG. 6D. A third conductive spacer is applied so as to overlay a portion of the gap formed by ablation in the first conductive layer as the conductive material of the first conductive layer, as shown in FIG. 6E, to establish an electrical connection between the first and second conductive layers of the ECM. A second substrate, as seen in FIG. 6F the inner facing surface of which is coated with an electrically conductive coating, is then laminated onto the spacers. The three different tracks, A, B, and C, of ECMs shown in FIG. 6F may be separated by cutting length-wise along lines I and II to form single continuous tracks of ECMs as shown in FIG. 6G. Each of the continuous tracks is then cut width-wise to form multiple, singulated ECMs as shown in FIG. 6H.

Preferably, the ECMs of the invention are not used in conjunction with a carrier. However, the ECMs may be incorporated with a carrier to provide additional structural integrity and facilitate handling. Suitable carriers are disclosed in U.S. patent application Ser. No. 13/090,620 incorporated in its entirety herein by reference. Such a carrier may be formed from any suitable material and preferably is formed from inexpensive materials, such as plastic or cardboard, that are non-conductive and that do not chemically react the ECM over time.

What is claimed is:

1. An electrochemical module, comprising:
a first substrate having a first conductive layer thereon and forming a first substrate-conductive layer assembly wherein the first substrate-conductive layer assembly has a first width and a first length;
a second substrate having a second conductive layer thereon and forming a second substrate-conductive layer assembly wherein the second substrate-conductive layer assembly has a second width that is less than the first width and a second length that is substantially the same as the first length, wherein the first and second conductive layers are in a facing relationship;
a first and a second spacer disposed between the first substrate-conductive layer assembly and second substrate-conductive layer assembly and maintaining the first substrate-conductive layer assembly and second substrate-conductive layer assembly in a spaced apart relationship, the first and second spacers extending along the first length;
a chamber formed between the first substrate-conductive layer assembly and second substrate-conductive layer assembly and configured to receive a fluid sample, the chamber comprising a first sidewall defined by a second latitudinal end of the first spacer and a second sidewall defined by a first latitudinal end of the second spacer, wherein the chamber comprises a reagent capable of reacting with an analyte in the fluid sample; and
a third spacer adjacent to and in physical contact with the second latitudinal end, opposite the first latitudinal end, of the second spacer, a surface of the third spacer comprising a conductive layer that is in a facing relationship and in electrically conductive contact with the second conductive layer, the third spacer extending along the first length.

2. The module of claim 1, wherein the first width of the first substrate-conductive layer assembly is about 3 mm to about 48 mm, and the first length of the first substrate-conductive layer assembly is about 0.5 mm to about 20 mm.

3. The module of claim 1 or 2, wherein the chamber comprises a size such that a fluid volume within the chamber is from about 0.1 micro-liters to about 5 micro-liters.

4. The module of claim 1, wherein the first and second conductive layers comprise a metal selected from the group consisting of gold, palladium, platinum, tin-oxide, iridium, indium, titanium-palladium alloys, and combinations thereof.

5. The module of claim 4, wherein the first and second conductive layers comprise the same metal.

6. The module of claim 1, wherein one of the first and second conductive layers comprises palladium and one of the first and second conductive layers comprises gold.

7. The module of claim 1, wherein the first and second conductive layers comprise a non-metal selected from the group consisting of carbon-based materials, carbon-based materials with electro-catalytic materials, graphene, and combinations thereof.

8. An electrochemical module, comprising:
a first substrate having a first conductive layer thereon, the first conductive layer comprising a first and second portion having a gap therebetween, the first substrate and first conductive layer forming a first substrate-conductive layer assembly wherein the first substrate-conductive layer assembly has a first width and a first length;
a second substrate having a second conductive layer thereon and forming a second substrate-conductive layer assembly wherein the second substrate-conductive layer assembly has a second width that is less than the first width and a second length that is substantially the same as the first length, wherein the first and second conductive layers are in a facing relationship;
a first and a second spacer disposed between the first substrate-conductive layer assembly and second substrate-conductive layer assembly and maintaining the first substrate-conductive layer assembly and second substrate-conductive layer assembly in a spaced apart relationship, the first and second spacers extending along the first length;
a chamber formed between the first substrate-conductive layer assembly and second substrate-conductive layer assembly and configured to receive a fluid sample, the chamber comprising a first sidewall defined by a second latitudinal end of the first spacer and a second sidewall defined by a first latitudinal end of the second spacer, wherein the chamber comprises a reagent capable of reacting with an analyte in the fluid sample; and
an electrically conductive third spacer adjacent to the second latitudinal end, opposite the first latitudinal end, of the second spacer, wherein the third spacer is in contact with at least a portion of the gap and in electrically conductive contact with the first and second conductive layers, the third spacer extending along the first length.

9. The module of claim 8, wherein the first width of the first substrate-conductive layer assembly is about 3 mm to about 48 mm, and the first length of the first substrate-conductive layer assembly is about 0.5 mm to about 20 mm.

10. The module of claim 8 or 9, wherein the chamber comprises a size such that a fluid volume within the chamber is from about 0.1 micro-liters to about 5 micro-liters.

11. The module of claim 8, wherein the first and second conductive layers comprise a metal selected from the group consisting of gold, palladium, platinum, tin-oxide, iridium, indium, titanium-palladium alloys, and combinations thereof.

12. The module of claim 11, wherein the first and second conductive layers comprise the same metal.

13. The module of claim 8, wherein one of the first and second conductive layers comprises palladium and one of the first and second conductive layers comprises gold.

14. The module of claim 8, wherein the first and second conductive layers comprise a non-metal selected from the group consisting of carbon-based materials, carbon-based materials with electro-catalytic materials, graphene, and combinations thereof.

15. The module of claim 1, wherein the first width of the first substrate-conductive layer assembly is about 6 mm to about 10 mm, and the first length of the substrate-conductive layer assembly is about 1 to 4 mm.

16. The module of claim 8, wherein the first width of the first substrate-conductive layer assembly is about 6 mm to about 10 mm, and the first length of the first substrate-conductive layer assembly is about 1 to 4 mm.

* * * * *